US00PP26687P2

(12) United States Plant Patent
Graff

(10) Patent No.: US PP26,687 P2
(45) Date of Patent: May 3, 2016

(54) ***HIBISCUS* PLANT NAMED 'LONGI TROPIC SOFT PINK'**

(50) Latin Name: *Hibiscus rosa-sinensis*
Varietal Denomination: Longi Tropic Soft Pink

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 124 days.

(21) Appl. No.: 14/120,537

(22) Filed: May 31, 2014

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — C. A. Whealy

(57) ABSTRACT

A new and distinct cultivar of *Hibiscus* plant named 'Longi Tropic Soft Pink', characterized by its upright, uniformly mounding and bushy plant habit; glossy dark green-colored leaves; uniform, continuous and freely flowering habit; large pink-colored flowers with dark red-colored centers; and excellent flower longevity.

2 Drawing Sheets

Botanical designation: *Hibiscus rosa-sinensis.*
Cultivar denomination: 'LONGI TROPIC SOFT PINK'.

BACKGROUND OF THE INVENTION

The present invention relates to a new and distinct cultivar of *Hibiscus* plant, botanically known as *Hibiscus rosa-sinensis,* and hereinafter referred to by the name 'Longi Tropic Soft Pink'.

The new *Hibiscus* plant is a product of a planned breeding program conducted by the Inventor in Sabro, Denmark. The objective of the breeding program is to create new compact, uniform, strong and freely-branching *Hibiscus* plants with continuous flowering and attractive long-lasting flowers.

The new *Hibiscus* plant originated from a cross-pollination conducted by the Inventor in October, 2006 in Sabro, Denmark of a proprietary selection of *Hibiscus rosa-sinensis* identified as code number GB-2006-0001, not patented, as the female, or seed, parent with *Hibiscus rosa-sinensis* 'Camaro Wind', not patented, as the male, or pollen, parent. The new *Hibiscus* plant was discovered and selected by the Inventor as a flowering plant within the progeny of the stated cross-pollination in a controlled greenhouse environment in Sabro, Denmark in August, 2007.

Asexual reproduction of the new *Hibiscus* plant by vegetative terminal cuttings in a controlled greenhouse environment in Sabro, Denmark since October, 2007 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Longi Tropic Soft Pink'. These characteristics in combination distinguish 'Longi Tropic Soft Pink' as a new and distinct *Hibiscus* plant:

1. Upright, uniformly mounding and bushy plant habit.
2. Shiny dark green-colored leaves.
3. Uniform, continuous and freely flowering habit.
4. Large pink-colored flowers with dark red-colored centers.
5. Excellent flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* have narrower leaves than plants of the female parent selection.
2. Plants of the new *Hibiscus* have larger flowers than plants of the female parent selection.
3. Plants of the new *Hibiscus* and the female parent selection differ in flower color as plants of the female parent selection have red-colored flowers.
4. Flowers of plants of the new *Hibiscus* are longer-lasting than flowers of plants of the female parent selection.

Plants of the new *Hibiscus* can be compared to plants of the male parent, 'Camaro Wind'. Plants of the new *Hibiscus* differ primarily from plants of 'Camaro Wind' in the following characteristics:

1. Plants of the new *Hibiscus* have broader leaves than plants of 'Camaro Wind'.
2. Plants of the new *Hibiscus* have larger flowers than plants of 'Camaro Wind'.
3. Plants of the new *Hibiscus* and 'Camaro Wind' differ in flower color as plants of 'Camaro Wind' have red-colored flowers.
4. Flowers of plants of the new *Hibiscus* are longer-lasting than flowers of plants of 'Camaro Wind'.

Plants of the new *Hibiscus* can be compared to plants of the *Hibiscus rosa-sinensis* 'Adonis', disclosed in U.S. Plant Pat. No. 21,592. In side-by-side comparisons conducted in Sabro, Denmark, plants of the new *Hibiscus* differed from plants of 'Adonis' in the following characteristics:

1. Plants of the new *Hibiscus* and 'Adonis' differed in leaf shape.
2. Plants of the new *Hibiscus* and 'Adonis' differed in flower color as plants of 'Adonis' had darker pink-colored flowers.
3. Flowers of plants of the new *Hibiscus* were longer-lasting than flowers of plants of 'Adonis'.

Plants of the new *Hibiscus* can be compared to plants of the *Hibiscus rosa-sinensis* 'Juno', disclosed in U.S. Plant patent application Ser. No. 13/694,674. In side-by-side comparisons conducted in Sabro, Denmark, plants of the new *Hibiscus* differed from plants of 'Juno' in the following characteristics:

1. Plants of the new *Hibiscus* and 'Juno' differed in leaf shape.
2. Plants of the new *Hibiscus* and 'Juno' differed in flower color as plants of 'Juno' had red purple-colored flowers.
3. Flowers of plants of the new *Hibiscus* were not as long-lasting as flowers of plants of 'Juno'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Longi Tropic Soft Pink' grown in a container.

The photograph on the second sheet is a close-up view of typical developing flower buds and a typical open flower of 'Longi Tropic Soft Pink'.

DETAILED BOTANICAL DESCRIPTION

The aforementioned photographs and following observations, measurements and values describe plants grown during the autumn and winter in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time about nine to ten weeks after planting. Plants were 25 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Longi Tropic Soft Pink'.

Parentage:

*Female, or seed, parent.*—Proprietary selection of *Hibiscus rosa-sinensis* identified as code number GB 2006-0001, not patented.

*Male or pollen parent.*—*Hibiscus rosa-sinensis* 'Camaro Wind', not patented.

Propagation:

*Type.*—By vegetative terminal cuttings.

*Time to initiate roots, summer and winter.*—About four weeks at temperatures about 24° C.

*Time to produce a rooted young plant, summer.*—About nine weeks at temperatures about 24° C.

*Time to produce a rooted young plant, winter.*—About ten weeks at temperatures about 24° C.

*Root description.*—Medium in thickness, fleshy; color, close to 158A.

*Rooting habit.*—Freely branching; dense.

Plant description:

*Plant and growth habit.*—Upright, uniformly mounding and bushy plant habit; moderately vigorous growth habit.

*Branching habit.*—Freely branching habit with usually about four to six lateral branches developing per plant; pinching enhances lateral branch development.

*Plant height.*—About 35 cm to 55 cm.

*Plant diameter* (*area of spread*).—About 30 cm to 50 cm.

Lateral branch description:

*Length.*—About 15 cm to 25 cm.

*Diameter.*—About 3 mm to 7 mm.

*Internode length.*—About 1 cm to 5 cm.

*Strength.*—Strong.

*Texture.*—Smooth, glabrous; with development, becoming woody.

*Color, developing.*—Close to 147A.

*Color, developed.*—Close to N199A.

Leaf description:

*Arrangement.*—Alternate, single; numerous.

*Length.*—About 8 cm to 12 cm.

*Width.*—About 5 cm to 7 cm.

*Shape.*—Ovate.

*Apex.*—Acuminate.

*Base.*—Obtuse to attenuate.

*Margin.*—Crenate; undulate.

*Texture, upper surface.*—Smooth, glabrous; venation, recessed.

*Texture, lower surface.*—Scattered pubescence; venation, prominent.

*Luster, upper surface.*—Glossy.

*Luster, lower surface.*—Slightly glossy.

*Venation pattern.*—Pinnate; arcuate.

*Color.*—Developing leaves, upper surface: Close to 147A. Developing leaves, lower surface: Close to 146A. Fully expanded leaves, upper surface: Close to N189A; venation, close to 146B. Fully expanded leaves, lower surface: Close to 147A; venation, close to 146C.

*Petioles.*—Length: About 3 cm to 5 cm. Diameter: About 2 mm. Texture, upper and lower surfaces: Pubescent. Color, upper surface: Close to 146B. Color, lower surface: Close to 146C.

Flower description:

*Flower arrangement.*—Flowers arranged singly at terminal leaf axils; uniform, continuous and freely flowering habit with numerous flower buds and open flowers per plant at one time; flowers face mostly upright to slightly outwardly.

*Fragrance.*—None detected.

*Natural flowering season.*—Plants flower in the garden during the spring and summer or during periods of warm weather; in the greenhouse, plants can be flowered year-round; plants begin flowering about 10 to 14 weeks after pinching.

*Flower longevity.*—Excellent flower longevity, flowers last about four to five days on the plant; flowers persistent.

*Flower diameter.*—About 14 cm to 18 cm.

*Flower length* (*height*).—About 9 cm to 10 cm.

*Flower buds.*—Length: About 5 cm to 7 cm. Diameter: About 1.5 cm to 2 cm. Shape: Lanceolate. Color: Close to 35C and 1B.

*Petals.*—Arrangement: Five imbricate petals in a single whorl. Length: About 9 cm to 11 cm. Width: About 8 cm to 10 cm. Shape: Fan-shaped. Apex: Rounded. Base: Attenuate. Margin: Entire, slightly undulate. Texture, upper surface: Glabrous, rugose; venation, slightly prominent. Texture, lower surface: Glabrous, rugose; venation, prominent. Luster, upper and lower surfaces: Matte. Color: When opening, upper surface: Close to 55B; towards the base, close to 59A. When opening, lower surface: Close to 52D. Fully opened, upper surface: Close to between 55B and 65A; towards the base, close to 53A; venation, close to 55D; with development, main color becoming closer to 55B. Fully opened, lower surface: Close to 55B to 55C; venation, close to 56D; color does not change with development.

*Sepals.*—Appearance: Five sepals fused into a campanulate-shaped calyx. Length: About 3 cm. Width: About 1 cm to 1.2 cm. Shape: Lanceolate. Apex: Acuminate. Margin: Entire. Texture, upper surface: Rugose, pubescent; venation, prominent. Texture, lower surface: Slightly pubescent; venation, recessed. Luster, upper surface: Matte. Luster, lower surface: Slightly glossy. Color, upper surface: Close to 144A. Color, lower surface: Close to 144B.

*Peduncles.*—Length: About 3 cm to 5 cm. Diameter: About 2 mm to 3 mm. Strength: Strong. Texture: Sparsely pubescent. Color: Close to 143B.

*Reproductive organs.*—Androecium: Stamen number: Numerous, about 100. Staminal column length: About 7 cm. Staminal column color: Towards the base, close to 53A; mid-section, close to 53B; and towards the apex, close to 53C. Filament length: About 2.5 mm to 3 mm. Filament color: Close to 58B. Anther shape: Ovate, rounded. Anther length: About 1 mm to 2 mm. Anther color: Close to 29B. Amount of pollen: Abundant. Pollen color: Close to 21B. Gynoecium: Pistil length (including staminal column): About 9 cm. Style texture: Smooth, waxy. Style color: Close to 1D. Stigma appearance: Five-parted, rounded. Stigma color: Close to 41B. Ovary color: Close to 154D.

*Seeds and fruits.*—Seed and fruit development have not been observed on plants of the new *Hibiscus*.

Temperature tolerance: Plants of the new *Hibiscus* have been observed to have tolerate temperatures from about 1° C. to about 30° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Longi Tropic Soft Pink' as illustrated and described.

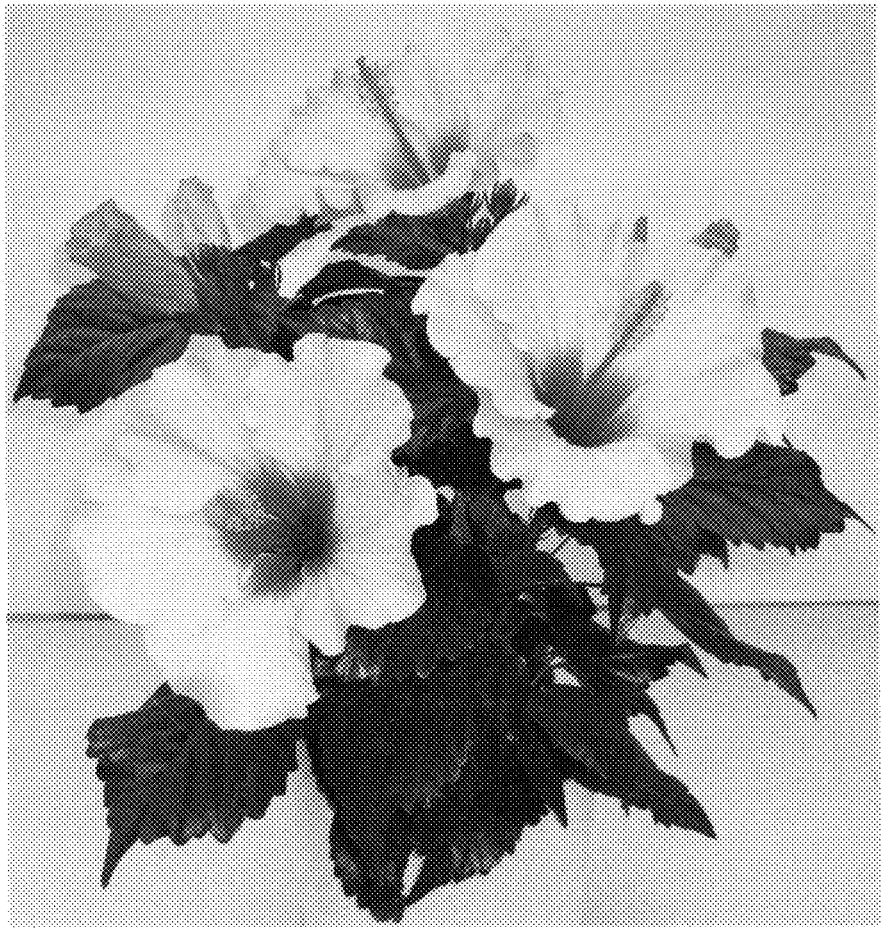

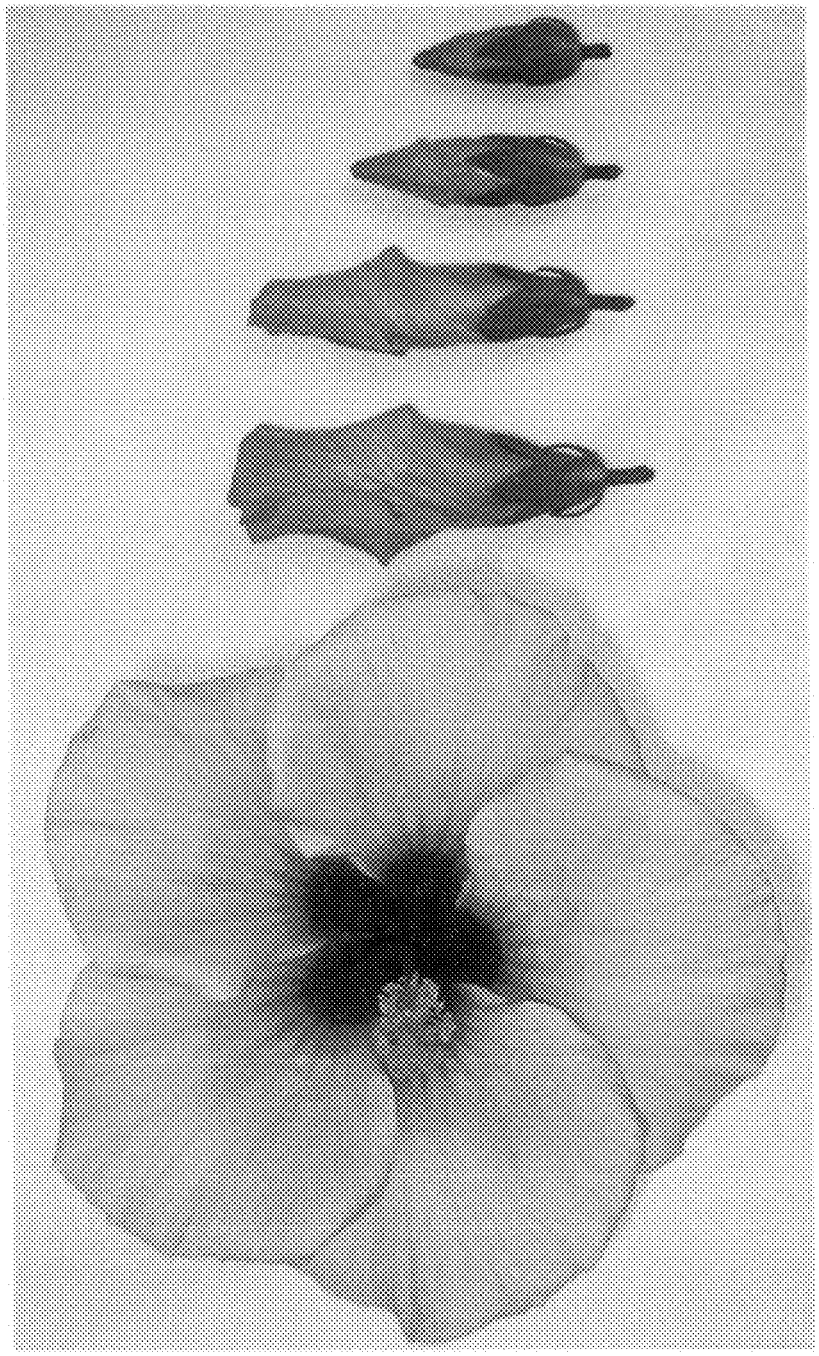

* * * * *